(12) United States Patent
Najjar

(10) Patent No.: US 11,918,505 B1
(45) Date of Patent: Mar. 5, 2024

(54) PENIS ENLARGEMENT DEVICE

(71) Applicant: Baseem Najjar, Lewes, DE (US)

(72) Inventor: Baseem Najjar, Lewes, DE (US)

( * ) Notice: Subject to any disclaimer, the term of this patent is extended or adjusted under 35 U.S.C. 154(b) by 0 days.

(21) Appl. No.: 18/473,248

(22) Filed: Sep. 24, 2023

(51) Int. Cl.
*A61F 5/41* (2006.01)

(52) U.S. Cl.
CPC ........... *A61F 5/41* (2013.01); *A61F 2005/411* (2013.01)

(58) Field of Classification Search
CPC ........ A61F 2005/411; A61F 5/41; A61F 6/02; A61F 2006/047; A61F 5/451; A61H 19/32; A61H 2201/1645
See application file for complete search history.

(56) References Cited

U.S. PATENT DOCUMENTS

| | | | |
|---|---|---|---|
| 2005/0124854 A1* | 6/2005 | Suchy | A61H 1/0218 600/39 |
| 2016/0235580 A1* | 8/2016 | Trost | A61F 5/41 |

FOREIGN PATENT DOCUMENTS

| | | | | |
|---|---|---|---|---|
| WO | WO-9626691 A1 * | 9/1996 | ............... | A61F 5/41 |
| WO | WO-2021160163 A1 * | 8/2021 | ........... | A61K 31/215 |

* cited by examiner

*Primary Examiner* — Ophelia A Hawthorne
(74) *Attorney, Agent, or Firm* — Sam Pierce

(57) ABSTRACT

According to an aspect of the present invention, there is provided a device for enlargement of the penis of a user, comprising: a bottom semi-circular member; a first hinge arranged on one side of the bottom semi-circular member; a second hinge arranged on the other side of the bottom semi-circular member; a first rod connecting to the first hinge; a second rod connecting to the second hinge; a middle bracket; and a top bracket, wherein the middle bracket connects the first rod to the second rod; and wherein the top bracket also connects the first rod to the second rod to stabilize the device; and wherein the first and second rods are configured to allow changing the length of the device and amount of stretching force on the penis of the user.

8 Claims, 1 Drawing Sheet

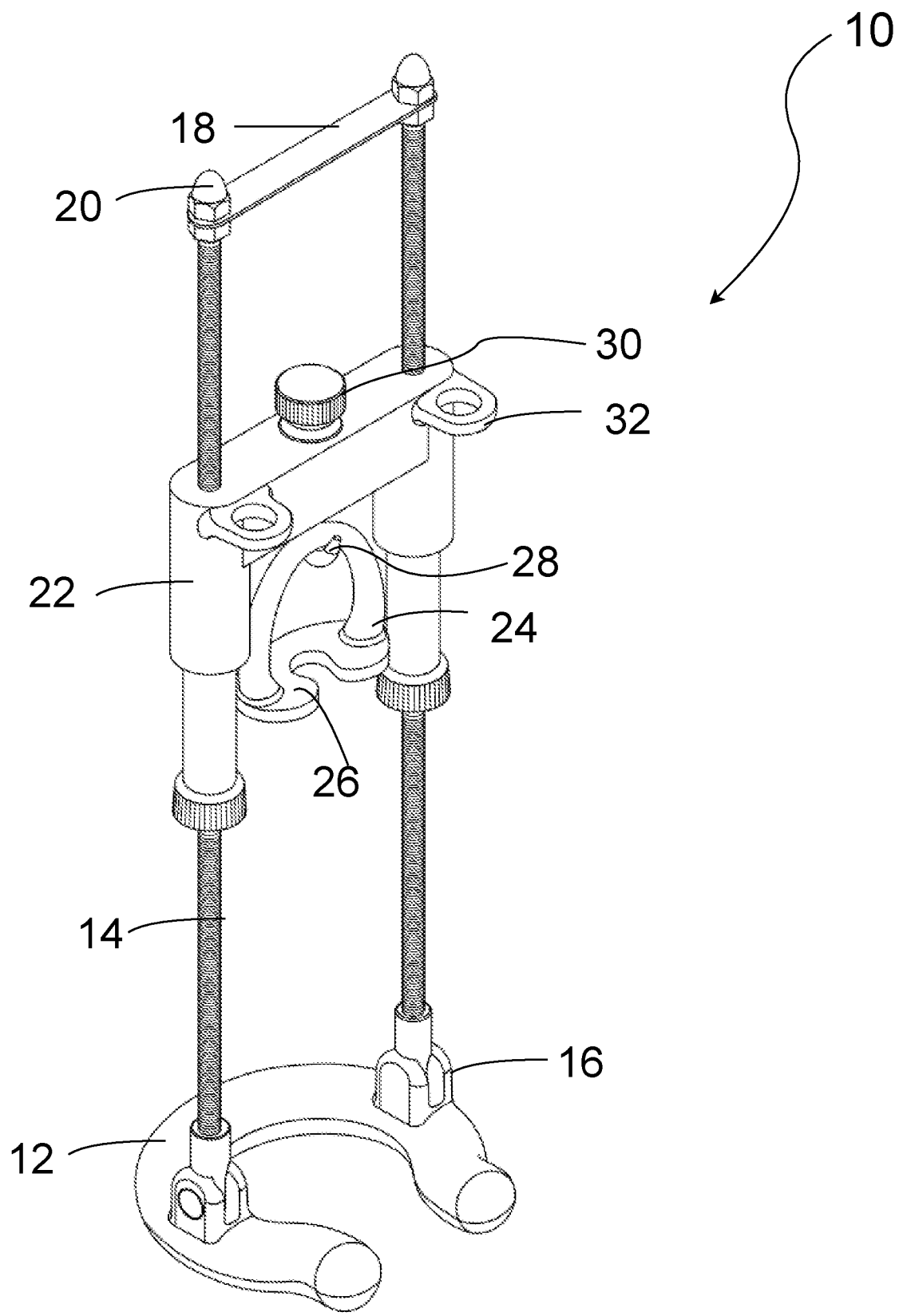

PENIS ENLARGEMENT DEVICE

BACKGROUND

Methods and devices for enhancing the penis of a male individual are well-known in the patent literature.

For example, US20150202109 discloses a penis enlargement device comprising a substantially flat member with a hole and neck adapted to fit over a human penis to be positioned flat against a user's lower abdomen; a ring member also adapted to fit around the base of the penis; a waist strap attached to said flat member adapted to hold the flat member in place; a substantially cylindrical cover attached to said neck adapted to connect to either stretch cords or to a weight container; whereby, weight or force is applied to the base of the penis causing the penis to enlarge over time.

U.S. Pat. No. 7,802,577 discloses a harness for stretching the penis, includes a belt for encircling the waist of the user, with a fastening mechanism secured to a rear part of the belt. A first tractive means applies tractive forces at the base of the penis of a user of the harness, and is secured to the belt via the fastening mechanism. A second tractive means applies tractive forces at the edge of the head of the penis of a user of the harness, and is also secured to the belt via the fastening mechanism. The first tractive means and the second tractive means apply a stretching force to the penis of the user of the harness.

U.S. Pat. No. 8,075,473 discloses an extension device for permanent penis enlargement and straightening via long-term elongation, the extension device comprising: a fastening means for application to a penis, the fastening means having an accommodation body, the accommodation body: being dimensionally stable, accommodating a glans penis of the penis over the entire surface of the glans penis when the glans penis is inserted into the extension device, having an inner contour essentially corresponding to a shape of the glans penis, having an opening for allowing insertion of the glans penis, and having an inner surface; a pulling apparatus connected to the fastening means; an elastic tube seal connected to the opening of the accommodation body; and a lubricant located on the inner surface of the accommodation body; wherein the pulling apparatus is formed by: a support, strap, belt or other clothing accessory or piece of clothing, the support, strap, belt or other clothing accessory or piece of clothing being connected to the accommodation body, being held on a body of the user, and being used as a stop, a stationary object, a frame supported on a body of the user, the frame being adjustable in length, or a weight attached to the accommodation body.

Nonetheless, prior art methods and devices suffer from significant drawbacks, including physical danger and inefficiency in bringing about the desired penile enlargement.

SUMMARY OF INVENTION

Therefore, the present invention provides an improved device for enlarging the penis of a user.

According to one aspect of the present invention disclosed herein, there is provided a device for enlargement of the penis of a user, comprising: a bottom semi-circular member; a first hinge arranged on one side of the bottom semi-circular member; a second hinge arranged on the other side of the bottom semi-circular member; a first rod connecting to the first hinge; a second rod connecting to the second hinge; a middle bracket; and a top bracket, wherein the middle bracket connects the first rod to the second rod; and wherein the top bracket also connects the first rod to the second rod to stabilize the device; and wherein the first and second rods are configured to allow changing the length of the device and amount of stretching force on the penis of the user.

According to one of yet another aspects of the present invention disclosed herein, there is provided a method of enlarging the penis of a user, comprising: positioning a bottom semi-circular member at the base of the penis of the user; providing a first hinge arranged on one side of the bottom semi-circular member; providing a second hinge arranged on the other side of the bottom semi-circular member; providing a first rod connecting to the first hinge; providing a second rod connecting to the second hinge; providing a middle bracket, wherein the middle bracket connects the first rod to the second rod; providing an adjustment mechanism to lengthen or shorten the exposed portions of the first and second rods; and changing the length of the device and amount of stretching force on the penis of the user by using the adjustment mechanism.

BRIEF DESCRIPTION OF THE DRAWINGS

FIG. 1 illustrates a device according to an embodiment of the present invention.

DETAILED DESCRIPTION

An embodiment illustrative of the present invention will be described with reference to the attached drawing.

FIG. 1 illustrates penis enlargement device according to an embodiment of the present invention.

Device 10 refers to the penis enlargement device according to an embodiment of the present invention as a whole.

Bottom semi-circular member 12 is a silicone padded base that sits on the base of the penis.

Rod 14 is one of the two rods on either side that allow for changing the length of the device and the stretching force applied to the penis of a user of the device.

Hinge 16 is one of two hinges on either side that allow, by bending rod 14 and its counterpart rod on the other side, for the device to bend 180 degrees to stretch the penis of a user of the device at any angle.

Top bracket 18 helps stabilize rod 14 and its counterpart rod on the other side to prevent unwanted twisting of the device.

Washer 20 secures top bracket 18 in place by connecting with another hex under the bracket.

Middle bracket 22 connects rod 14 and its counterpart. A user can gauge the tension on the penis by a meter on middle bracket 22. The number that is visible is the current tension of the device.

Cup holder and adapter ring 24 allows for the device to be used with a penis extender cup. A penis extender cup can be used with the device of embodiments to maximize the penis enlargement experience by a user of the device.

Cup holder and adapter base 26 is base of the cup holder and adapter which allows for the device to be used with a penis extender cup.

Hook 28 holds the vacuum cups that attach to the head of the penis when operation of the device is active.

Knob 30 allows for twisting hook 28 so that a user can stretch the penis of the user while also twisting the penis.

Hole 32 and its counterpart on the other side can hold the strap that helps secure the device in one direction.

The embodiments described above are given merely for example and for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A device for enlargement of the penis of a user, comprising:
   a hook for holding vacuum cups that attach to the head of the penis;
   a bottom semi-circular member;
   a first hinge arranged on one side of the bottom semi-circular member;
   a second hinge arranged on the other side of the bottom semi-circular member;
   a first rod connecting to the first hinge;
   a second rod connecting to the second hinge;
   a middle bracket; and
   a top bracket,
   wherein the middle bracket connects the first rod to the second rod; and
   wherein the top bracket also connects the first rod to the second rod to stabilize the device; and
   wherein the first and second rods are configured to allow changing the length of the device and amount of stretching force on the penis of the user.

2. The device of claim 1, wherein the first hinge and the second hinge bend the first rod and the second rod up to 180 degrees to stretch the penis of the user at any angle.

3. The device of claim 1, further comprising an adapter for a cup holder.

4. The device of claim 1, further comprising extensions from the middle bracket having holes for a strip for further securing the device.

5. The device of claim 1, wherein the bottom semi-circular member is a silicone padded base.

6. The device of claim 1, wherein the top bracket is secured by a first hex under the bracket and a second hex on top of the bracket.

7. The device of claim 1, further comprising a meter for displaying the current tension on the penis of a user.

8. The device of claim 1, wherein the rods are configured to change the length of the device by having a hollow region within the middle bracket for the rods to move in a direction that lengthens or shortens the device.

* * * * *